(12) United States Patent
Dellis et al.

(10) Patent No.: US 7,714,163 B2
(45) Date of Patent: May 11, 2010

(54) PROCESS FOR PREPARING QUATERNARY ACID AND AMMONIUM SALTS

(75) Inventors: Philippe Dellis, Dijon (FR); Kamel Nasar, Mirebeau sur Beze (FR)

(73) Assignee: Fournier Laboratories Ireland Ltd., Cork (IE)

( * ) Notice: Subject to any disclaimer, the term of this patent is extended or adjusted under 35 U.S.C. 154(b) by 0 days.

(21) Appl. No.: 12/110,667

(22) Filed: Apr. 28, 2008

(65) Prior Publication Data

US 2008/0275270 A1 Nov. 6, 2008

Related U.S. Application Data

(63) Continuation of application No. PCT/FR2006/051118, filed on Oct. 27, 2006.

(30) Foreign Application Priority Data

Oct. 28, 2005 (FR) .................. 05 11103

(51) Int. Cl.
C07C 59/00 (2006.01)
(52) U.S. Cl. .................... 562/471
(58) Field of Classification Search .......... None
See application file for complete search history.

(56) References Cited

U.S. PATENT DOCUMENTS

| 3,897,485 A | 7/1975 | Meunier |
| 4,739,101 A | 4/1988 | Bourgogne et al. |
| 2005/0148594 A1 | 7/2005 | Cink et al. |

FOREIGN PATENT DOCUMENTS

| EP | 0 245 156 A1 | 11/1987 |
| EP | 0 521 393 A2 | 1/1993 |
| WO | 9616016 | * 5/1996 |
| WO | WO 96/16016 A1 | 5/1996 |
| WO | WO 02/090307 A1 | 11/2002 |

OTHER PUBLICATIONS

Davis et al., Synthesis (2004), (12), 1959-1962.*
Berry et al., Dalton Transactions (2003), (22), 4297-4302.*
International Search Report dated Mar. 28, 2007 w/English translation of pertinent portion (five (5) pages).

* cited by examiner

*Primary Examiner*—Karl J Puttlitz
(74) *Attorney, Agent, or Firm*—Crowell & Moring LLP

(57) ABSTRACT

A process for preparing a quaternary ammonium salt of a fibric acid, represented by the following reaction scheme:

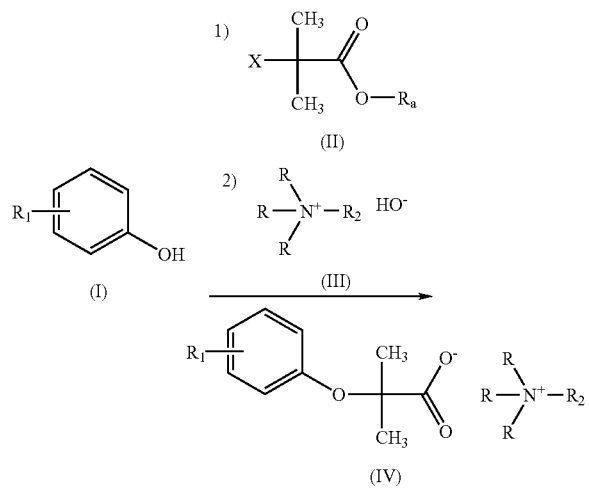

is carried out in a single operation starting from a phenol of formula (I), an α-halogenated ester of formula (II) and a quaternary ammonium hydroxide of formula (III). This process makes it possible economically to prepare a choline salt of fenofibric acid in high purity that can be used directly as the active substance in a pharmaceutical composition intended for human consumption.

13 Claims, No Drawings

PROCESS FOR PREPARING QUATERNARY ACID AND AMMONIUM SALTS

CROSS REFERENCE TO RELATED APPLICATIONS

This application is a continuation of international patent application no. PCT/FR2006/051118, filed Oct. 27, 2006 designating the United States of America, and published in French on May 3, 2007 as WO 2007/048986, the entire disclosure of which is incorporated herein by reference. Priority is claimed based on French patent application no. FR 0 511 103, filed Oct. 28, 2005.

BACKGROUND OF THE INVENTION

The invention relates to a novel process for the synthesis of a salt of an organic acid and a base, especially a salt of an acid of the fibrate family and a base of the quaternary ammonium type, and more particularly the salt of fenofibric acid and choline.

PRIOR ART

Fenofibrate

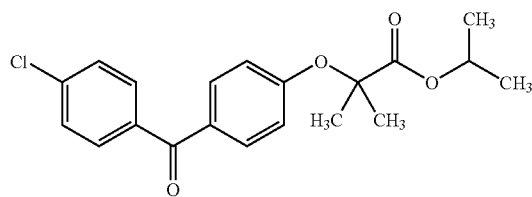

is a known active substance for treating hypertriglyceridemia and hyper-cholesterolemia. This compound is an isopropyl ester, but in a biological medium the ester is rapidly hydrolyzed to give fenofibric acid, which is the active metabolite of fenofibrate.

It has recently been proposed (US 2005/0148594) to treat these diseases using a galenical formulation containing fenofibric acid itself as the active substance, and particularly preferably using a salt of fenofibric acid and an organic base, especially choline. The preparation of the choline salt is described in Examples 17A and 17B of the document cited above, and consists in using fenofibric acid as the starting compound and salifying it with choline hydroxide, which is used in the form of a solution in methanol.

The currently most economic process for the preparation of fenofibric acid consists in hydrolyzing fenofibrate, which is a commercial product and can be manufactured e.g. by reacting 4-chloro-4'-hydroxybenzophenone with isopropyl 2-bromo-2-methylpropanoate (EP0245156B1).

Preparations of choline salts are also described in the literature. For example, U.S. Pat. No. 3,897,485 describes the preparation of a salt with a dialkylacetic acid by combining the choline base with the acid. Likewise, published PCT application no. WO 96/16016 describes the preparation of a salt of ketoprofen and choline and European patent application no. EP 521,393 describes the preparation of a salt of diclofenac and choline, the processes recommended in these documents again using the acid as the starting material.

SUMMARY OF THE INVENTION

The present invention relates to a novel economic process for the preparation of a quaternary ammonium salt of a fibric acid of formula (IV), as defined below, which is capable of yielding, in a single operation, a product of high purity that is compatible with use in human therapeutics.

This process consists essentially in reacting an α-halogenated ester of 2-methylpropanoic acid (II) with a substituted phenol (I) and then, without isolating the intermediate formed, with a base of the quaternary ammonium type (III), and can be represented by the following reaction scheme:

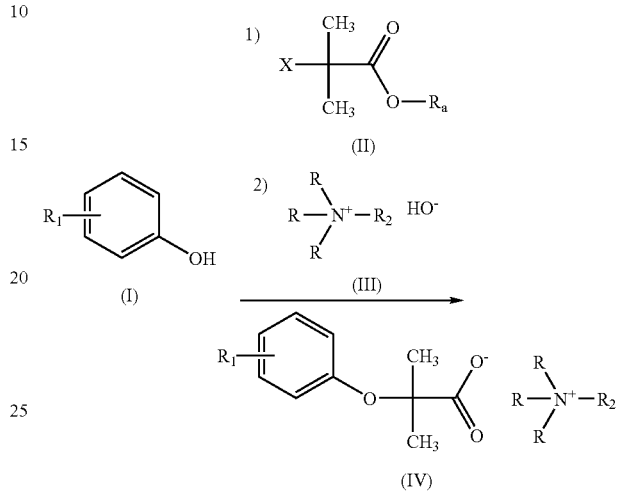

in which:

$R_1$ is a chlorine atom, a 2-(4-chlorobenzoylamino)ethyl group, a 4-chlorobenzoyl group or a 2,2-dichlorocyclopropyl group and is preferably located in the para-position relative to the OH group, X is a halogen, preferably a bromine atom, $R_a$ is a linear or branched $C_1$-$C_6$ alkyl group, $R_2$ is a linear or branched $C_1$-$C_4$ alkyl group or a linear or branched $C_1$-$C_4$ hydroxyalkyl group, and R is a linear $C_1$-$C_3$ alkyl group.

Thus the originality of the process according to the present invention consists in reacting a fibric acid precursor with a quaternary ammonium hydroxide in a single operation, i.e. without isolating the intermediate formed. Totally unexpectedly, a quaternary ammonium salt of fibrin acid is thus obtained directly with a very high purity in excess of 99.5% and can be used, without further purification, as the active substance of a drug for use in humans.

This process is particularly valuable for the preparation of a quaternary ammonium salt of fenofibric acid, especially a salt of fenofibric acid and choline.

In fact, in this case, in contrast to the currently known preparative processes, it is not necessary to use as the starting material a fenofibric acid originating from the hydrolysis of fenofibrate. The resulting process is consequently simpler to carry out and more economic.

In general, the process according to the present invention makes it possible in particular to prepare a quaternary ammonium salt of a fibric acid of the formula

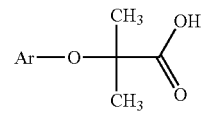

in which Ar is a phenyl group substituted in the para position by a chlorine atom (in which case it is clofibric acid), a 4-chlorobenzoyl group (in which case it is fenofibric acid), a 2-(4-chlorobenzoylamino)ethyl group (in which case it is bezafibrate) or a 2,2-dichlorocyclopropyl group (in which case it is ciprofibrate).

Within the scope of the present patent application, linear or branched $C_1$-$C_6$ alkyl group is understood as meaning a linear or branched, saturated hydrocarbon chain containing 1 to 6 carbon atoms, selected e.g. from methyl, ethyl, propyl, butyl, 1-methylethyl, 1-methylpropyl, 2-methylpropyl, 1,1-dimethylethyl, pentyl and hexyl groups.

$C_1$-$C_4$ hydroxyalkyl group is understood as meaning an alkyl chain containing 1 to 4 carbon atoms, such as defined above, and carrying at least one OH group bonded directly to any one of the carbon atoms.

In general, the chemical reactions involved in carrying out the process according to the invention can be performed either in the presence of a solvent, or in the absence of a solvent, or, advantageously, in the presence of a solvent for the second reaction. In fact, the final step of the process must advantageously be performed in the presence of a solvent, preferably in the presence of an alcohol, to give a compound of high purity.

In one preferred embodiment of the invention, a single solvent will be used for the final reaction and the purification of the salt produced. In particular, this solvent is a linear or branched propanol. Under these conditions the purity of the salt obtained is greater than 99.5% when assayed by HPLC (high performance liquid chromatography) for the acid content and by potentiometry for the quaternary ammonium content.

According to one particular characteristic, the process according to the invention comprises:

reacting a phenol of formula (I) with an α-halogenated ester of formula (II), advantageously used in excess relative to stoichiometric conditions, in the presence of a base, at a temperature between 80 and 160° C., for a period of 1 to 8 hours; then reacting a quaternary ammonium hydroxide of formula (III) with the resulting reaction medium, in the presence of a solvent, preferably after removal of the insoluble mineral compounds, at a temperature between 80 and 120° C., for a period of 1 to 5 hours; and separating out the resulting salt of formula (IV) which forms.

Advantageously, the above-mentioned solvent is a linear or branched propanol (n-propanol or isopropanol).

The process according to the present invention makes it possible in particular to prepare a quaternary ammonium salt of fenofibric acid by using the compound of formula (I) in which $R_1$ is a 4-chlorobenzoyl group in the 4-position relative to the hydroxyl group, a compound of formula (II) in which $R_a$ is a linear or branched $C_1$-$C_3$ alkyl group and the compound of formula (III) in which R is a methyl group and $R_2$ is a 2-hydroxyethyl group.

One preferred embodiment of the invention comprises reacting 4-chloro-4'-hydroxybenzophenone with ethyl or (iso)propyl 2-bromo-2-methylpropanoate and then adding choline hydroxide to give the choline salt of fenofibric acid directly, i.e. without isolation of the intermediate formed, in a one-pot operation.

In one general embodiment of the process according to the invention, the first step is to prepare a mixture of the phenol of formula I, as defined above, with a stoichiometrically at least equivalent amount of the ester of formula II in which X is a halogen, preferably a bromine atom, and $R_a$ is a linear or branched $C_1$-$C_6$ alkyl group. As the ester of formula II is a liquid at room temperature, it is not generally necessary to use a solvent at this stage of the process. However, if the reactor used does not allow sufficient agitation, it is entirely possible to carry out the reaction in the presence of a solvent such as an alcohol or a ketone, without these two examples implying a limitation. It will nevertheless be preferable in this case to use a solvent whose boiling point is at least 80° C. at atmospheric pressure.

The mixture of starting reactants is then heated to a temperature between 80 and 160° C. and a mineral base is added gradually, preferably in a substantially equimolar amount relative to the compound of formula I. This base is e.g. sodium or potassium carbonate or bicarbonate or calcium carbonate. This base can be added in the form of powder or pellets, said products generally being solid, but it can also be added in the form of a highly concentrated solution or a suspension in water. The rate of addition is conventionally fairly rapid and is limited only by the evolution of the carbon dioxide produced by the reaction.

The reaction time is between 1 hour and 8 hours, during which the water introduced or formed by the reaction is preferably removed by distillation.

According to one particular characteristic, a solvent for the organic compounds contained in the medium is then added and a hot filtration is advantageously carried out to remove the insoluble mineral compounds. This solvent is e.g. an alcohol, preferably a linear or branched propanol.

The solution, kept at the same temperature, is then brought into contact with the compound of formula III, in which $R_2$ is a linear or branched $C_1$-$C_4$ alkyl group or a linear or branched $C_1$-$C_4$ hydroxyalkyl group and R is a linear $C_1$-$C_3$ alkyl group. This compound can be introduced pure or in solution in an appropriate solvent such as, preferably, water or an alcohol.

The reaction mixture is agitated at a temperature between 80 and 120° C. for 1 to 5 hours.

If the compound of formula III has been introduced in the form of an aqueous solution, the water is then removed by azeotropic distillation.

The final mixture, in the form of a solution, is then filtered hot and subsequently cooled under conditions that allow the expected salt to crystallize, after which the crystals are filtered off on a filter or aspirator and dried.

If this process according to the invention is followed, the expected salt is generally obtained with a purity consistent with direct use in pharmaceutical compositions intended for human consumption, i.e. a purity of at least 99.5%.

The invention further relates to the salt with a purity in excess of 99.5% that is obtained by the process of the invention, and to its use in therapeutics for the manufacture of drugs for human medicine. These drugs are preferably formulated for oral absorption, e.g. in the form of capsules or tablets. These dry galenical preparations, in the form of lozenges, ordinary or film-coated tablets, or capsules, are obtained by methods known to those skilled in the art, for example by mixing the salt with excipients to give e.g. granules, which can be compressed or introduced into capsules. In one preferred embodiment of the invention, the pure salt is a quaternary ammonium salt of fenofibric acid present in an amount of between 40 and 180 mg per dosage unit. Preferably, the quaternary ammonium compound which forms the salt with fenofibric acid is choline.

The present invention will be understood more clearly from the description of the following embodiments, which are presented here in order to illustrate the invention and must not be considered as implying a limitation.

EXAMPLE I

2-[4-(4-Chlorobenzoyl)phenoxy]-2-methylpropanoic Acid Choline Salt

A mixture of 1108 g (5.28 mol) of isopropyl 2-bromo-2-methylpropanoate and 650 g (2.79 mol) of (4-chlorophenyl)(4-hydroxyphenyl)methanone is heated at 145° C. under a nitrogen atmosphere, with thorough stirring, in a 5 l reactor equipped for operation under reflux or distillation. 448 g (3.24 mol) of potassium carbonate are then added and the temperature of the reaction medium is raised to 155° C. The reaction mixture is stirred at this temperature for 4 hours. During this period the aqueous phase produced is collected in the distillate. The temperature of the reaction medium is reduced to 145° C. and the internal pressure of the reactor is lowered gradually so as to remove the excess brominated reactant by distillation. These conditions are maintained for about 2 hours, during which time all the distillates are collected in a receiver. The temperature of the mixture is then reduced to 120° C. and, with the reactor at atmospheric pressure, 1.95 l of propanol are added. The mixture is then at a temperature of about 80-90° C. and is filtered under nitrogen pressure. The residual solid is rinsed on the filter with about 0.75 l of hot propanol. The filtrates, maintained at the same temperature, are combined in the 5 l reactor and 790 g (2.93 mol) of a 45% aqueous solution of choline hydroxide are added gradually, followed by 0.80 l of propanol. The reaction mixture is then brought to the boil at atmospheric pressure and the distillate produced is collected until about 1.60 l of a propanol/water/isopropanol mixture have been obtained. The mixture is filtered on a clarifying filter and the filtrate is gradually cooled down to a temperature of about 10° C., with stirring, in order to crystallize the salt. The crystalline salt is separated off and washed with 0.65 l of cold propanol on an aspirator and then dried in an oven under reduced pressure.

This gives 824 g of the expected salt in the form of white crystals (yield=70%).

The purity of the salt obtained is checked by HPLC, the assay being performed by the method described for fenofibrate in the European Pharmacopeia or the US Pharmacopeia. The fenofibric acid can be assayed by chromatography against a reference sample. The choline present in the salt is assayed by potentiometry.

Analysis of the compound shows a purity in excess of 99.5% and the absence of impurities in a proportion greater than 0.1%.

M.p.=213° C.

EXAMPLE II

2-[4-(4-Chlorobenzoyl)phenoxy]-2-methylpropanoic Acid Choline Salt

A mixture of 100 g (0.43 mol) of (4-chlorophenyl)(4-hydroxyphenyl)-methanone and 148 g (0.82 mol) of methyl 2-bromo-2-methylpropanoate is prepared in a 1 l reactor maintained under a nitrogen atmosphere. The mixture is heated to 145° C., with thorough stirring, and 69 g (0.5 mol) of potassium carbonate are added. The reaction medium is maintained at 145° C. for 3 hours, with thorough stirring, during which time the water formed by the reaction is collected in the distillate. The pressure in the reactor is then gradually reduced in order to remove the excess brominated reactant by distillation. The mixture is then cooled to about 100° C. and 300 ml of n-propanol are added. The resulting mixture is stirred for 10 mm at 90° C. and then filtered at this temperature to remove the insoluble mineral salts. The residual solid is rinsed with 100 ml of hot n-propanol, which is combined with the previous filtrates. The solution obtained is placed in the 1 l reactor under a nitrogen atmosphere and 121.5 g (0.45 mol) of a 45% aqueous solution of choline hydroxide are added. The reaction mixture is stirred for 3 hours under gentle reflux of the solvent and about 240 ml of solvent are then distilled, 130 ml of n-propanol being added to the reactor. The reactor contents are subsequently filtered on a clarifying filter and then cooled slowly to about 15° C. The resulting suspension is filtered on an aspirator and the isolated solid is rinsed with 100 ml of cold n-propanol and then dried in a vacuum oven.

This gives 122 g of the expected salt in the form of a white crystalline solid (yield=67.5%).

The purity of the salt obtained is greater than 99.5%.

EXAMPLE III

2-[4-(4-Chlorobenzoyl)phenoxy]-2-methylpropanoic Acid Choline Salt

The reaction is carried out analogously to that described in Example II except that 159 g of ethyl 2-bromo-2-methylpropanoate are used.

This gives 127 g of the expected salt in the form of a white crystalline powder, this being a yield of 70%. The salt has a purity in excess of 99.8%.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A process for preparing a quaternary ammonium salt of a fibric acid corresponding to formula IV:

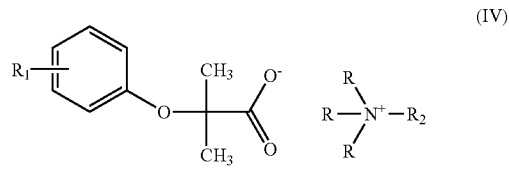

(IV)

wherein:
R$_1$ is a chlorine atom, a 2-(4-chlorobenzoylamino)ethyl group, a 4-chlorobenzoyl group or a 2,2-dichlorocyclopropyl group,
R$_2$ is a linear or branched C$_1$-C$_4$ alkyl group or a linear or branched C$_1$-C$_4$ hydroxyalkyl group, and
R is a linear C$_1$-C$_3$ alkyl group;
said process being represented by the following reaction scheme:

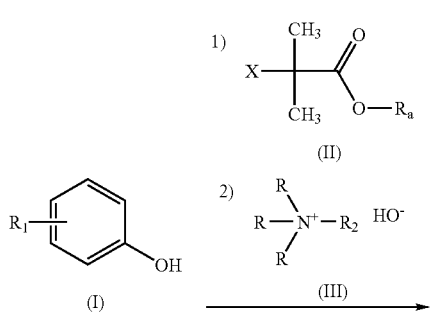

-continued

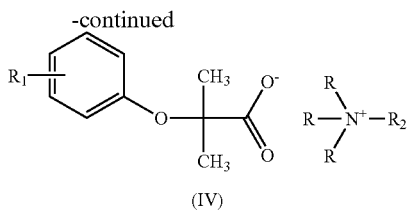
(IV)

and
said process being carried out as a one-pot reaction in a continuous procedure without any isolation of intermediates starting from:
  a phenol of formula (I), in which $R_1$ is as defined above,
  an α-halogenated ester of formula (II), in which X is a halogen and $R_a$ is a linear or branched $C_1$-$C_6$ alkyl group, and
  a quaternary ammonium hydroxide of formula (III), in which R and $R_2$ are as defined above.

2. A process according to claim 1, wherein, in the compound of formula (I) given above, $R_1$ is a 4-chlorobenzoyl group located in the para position relative to the oxygen.

3. A process according to claim 1, wherein, in the compound of formula (III) given above, R is a methyl group and $R_2$ is a 2-hydroxyethyl group.

4. A process according to claim 1, wherein, in the compound of formula (II) given above, X is a bromine atom.

5. A process according to claim 1, wherein said process comprises:
  reacting a phenol of formula (I) with an α-halogenated ester of formula (II), in the presence of a base, at a temperature between 80 and 160° C., for a period of 1 to 8 hours; then
  reacting a quaternary ammonium hydroxide of formula (III) with the resulting reaction medium, in the presence of a solvent, at a temperature between 80 and 120° C., for a period of 1 to 5 hours; and
  separating the resulting salt of formula (IV).

6. A process according to claim 5, wherein the α-halogenated ester of formula (II) is used in excess relative to stoichiometric conditions.

7. A process according to claim 5, wherein insoluble mineral compounds are removed from the reaction medium prior to reaction with the quaternary ammonium hydroxide of formula (III).

8. A process according to claim 5, wherein said solvent is a linear or branched propanol.

9. A process according to claim 5, wherein said process comprises:
  reacting a phenol of formula (I) with a stoichiometrically at least equivalent amount of an ester of formula (II) at a temperature between 80 and 160° C., in the presence of a mineral base, for a period of 1 to 8 hours,
  adding a solvent to the reaction medium,
  carrying out a hot filtration to remove insoluble mineral compounds,
  reacting the resulting solution with a quaternary ammonium hydroxide of formula (III) at a temperature between 80 and 120° C. for 1 to 5 hours, and
  filtering the mixture hot and subsequently cooling it under conditions that allow the expected salt to crystallize, after which the crystals are filtered out and dried to give the expected salt with a purity of at least 99.5%.

10. A process according to claim 9, wherein the added solvent is an alcohol.

11. A process according to claim 10, wherein the alcohol is a linear or branched propanol.

12. A process according to claim 9, wherein said mineral base is selected from the group consisting of sodium carbonate, potassium carbonate, sodium bicarbonate, potassium bicarbonate, and calcium carbonate.

13. A process according to claim 1, wherein $R_1$ is located in the para position relative to the oxygen bonded to the aryl ring.

\* \* \* \* \*